(12) United States Patent
Knoth

(10) Patent No.: US 8,863,480 B2
(45) Date of Patent: *Oct. 21, 2014

(54) PILL DISPENSER WITH INTERCHANGEABLE PLATEN HAVING ELECTRONICALLY READABLE/WRITABLE IDENTIFICATION

(75) Inventor: Norman D. Knoth, Clearwater, FL (US)

(73) Assignee: QEM, Inc., Largo, FL (US)

( * ) Notice: Subject to any disclaimer, the term of this patent is extended or adjusted under 35 U.S.C. 154(b) by 842 days.

This patent is subject to a terminal disclaimer.

(21) Appl. No.: 13/098,631

(22) Filed: May 2, 2011

(65) Prior Publication Data

US 2011/0208352 A1  Aug. 25, 2011

Related U.S. Application Data

(63) Continuation-in-part of application No. 12/163,615, filed on Jun. 27, 2008, now Pat. No. 7,958,701.

(51) Int. Cl.
*B65B 57/00* (2006.01)
*B65B 59/04* (2006.01)
*B65B 5/10* (2006.01)
*B65B 5/06* (2006.01)
*G06F 19/00* (2011.01)

(52) U.S. Cl.
CPC .............. *B65B 5/103* (2013.01); *G06F 19/3462* (2013.01)
USPC .......... 53/473; 53/475; 53/55; 53/493; 53/67; 53/168; 53/201; 53/246; 53/247; 221/121; 221/132; 269/58; 700/243

(58) Field of Classification Search
CPC ....................................................... B65B 5/103
USPC ......... 53/473, 475, 55, 493, 500, 501, 64, 67, 53/154, 168, 235, 237, 244, 246, 247, 248, 53/249, 255, 539, 201; 221/121, 124, 129, 221/132; 269/58; 700/240, 241, 243
See application file for complete search history.

(56) References Cited

U.S. PATENT DOCUMENTS

| 2,457,220 | A  | 12/1948 | Fowler et al. |
| 2,483,207 | A  | 9/1949  | Joseph |
| 3,091,067 | A  | 5/1963  | Ulucky et al. |
| 3,871,156 | A  | 3/1975  | Koenig et al. |
| 5,799,468 | A  | 9/1998  | Eck et al. |
| 6,318,051 | B1 | 11/2001 | Preiss |
| 6,497,342 | B2 | 12/2002 | Zhang et al. |
| 6,581,356 | B2 | 6/2003  | Kim |
| 6,805,259 | B2 | 10/2004 | Stevens et al. |
| 6,925,774 | B2 | 8/2005  | Peterson |

(Continued)

*Primary Examiner* — Stephen F Gerrity
(74) *Attorney, Agent, or Firm* — Larson & Larson, P.A.; Frank Liebenow; Justin P. Miller

(57) ABSTRACT

A device for dispensing pills includes a set of pill canisters and a control for releasing a desired quantity of pills from a selected pill canister at a target location. Several platens are provided; each of the platens has a platen identifier. A frame is situated beneath the target location. The frame is controlled to move in both an X axis and/or a Y axis and the frame holds a selected platen of a set of platens. The selected platen holds and supports a target container into which the desired quantity of pills is deposited. The platen identifier is read by the device for dispensing pills to determine which of the plurality of platens is in the frame.

14 Claims, 12 Drawing Sheets

(56) References Cited

U.S. PATENT DOCUMENTS

| | | |
|---|---|---|
| 7,006,894 B2 | 2/2006 | de la Huerga |
| 7,225,597 B1 | 6/2007 | Knoth |
| 7,334,379 B1 | 2/2008 | Seigel et al. |
| 7,426,814 B2 | 9/2008 | Knoth |
| 7,510,099 B2 | 3/2009 | Knoth |
| 7,587,878 B2 | 9/2009 | Kim |
| 7,637,078 B2 | 12/2009 | Ishiwatari et al. |
| 7,805,217 B2 | 9/2010 | Chudy et al. |
| 7,883,077 B2 | 2/2011 | Knoth |
| 7,886,506 B2 | 2/2011 | Knoth et al. |
| 7,908,827 B2 | 3/2011 | Knoth |
| 7,950,206 B2 * | 5/2011 | Knoth ............... 53/473 |
| 7,958,701 B2 * | 6/2011 | Knoth ............... 53/473 |
| 2006/0277870 A1 | 12/2006 | Feehan et al. |
| 2007/0145066 A1 | 6/2007 | Knoth |
| 2007/0157548 A1 | 7/2007 | Knoth |
| 2007/0251190 A1 | 11/2007 | Daigle et al. |
| 2008/0051937 A1 | 2/2008 | Khan et al. |
| 2008/0134637 A1 | 6/2008 | Boyer |
| 2008/0229718 A1 | 9/2008 | Feehan et al. |
| 2009/0044489 A1 | 2/2009 | Seigel |
| 2009/0188937 A1 | 7/2009 | Kim |
| 2009/0321469 A1 | 12/2009 | Knoth |
| 2009/0321470 A1 * | 12/2009 | Knoth ............... 221/7 |
| 2009/0321472 A1 * | 12/2009 | Knoth ............... 221/124 |

* cited by examiner

PILL DISPENSER WITH INTERCHANGEABLE PLATEN HAVING ELECTRONICALLY READABLE/WRITABLE IDENTIFICATION

This application is a continuation-in-part of U.S. application Ser. No. 12/163,615, filed Jun. 27, 2008, titled, "METHOD AND APPARATUS FOR AUTOMATICALLY FILLING PRESCRIPTIONS USING INTERCHANGEABLE PLATENS," U.S. Pat. No. 7,958,701, issued Jun. 14, 2011.

This application is related to U.S. Pat. No. 7,908,827, issued Mar. 22, 2011, "METHOD AND APPARATUS FOR AUTOMATICALLY FILLING PRESCRIPTIONS USING INTERCHANGEABLE PLATENS." Additionally, this application is related to U.S. Pat. No. 7,883,077 issued Feb. 8, 2011, titled, "LOW-PROFILE X-Y TABLE." Additionally, this application is related to U.S. Pat. No. 7,950,206, issued May 31, 2011, titled, "PILL DISPENSER WITH CANISTERS HAVING ELECTRONICALLY READABLE IDENTIFICATION.".

This application is related to U.S. Pat. No. 7,225,597 titled "MACHINE TO AUTOMATE DISPENSING OF PILLS," U.S. Pat. No. 7,510,099, titled "CASSETTE FOR DISPENSING PILLS," and U.S. Pat. No. 7,426,814, titled "METHOD OF DISPENSING PILLS FROM A MOVABLE PLATEN", all of which are incorporated by reference.

BACKGROUND OF THE INVENTION

1. Field

The present invention relates to the field of dispensing medicine and more particularly to an apparatus that automatically fills vials and blister packs with medicine in the form of pills, capsules, gel-caps and the like.

2. Background

The dispensing of medicine in the form of pills, capsules, gel-caps, and the like is performed in many ways and in many locations including pharmacies, packaging plants and hospitals. Pharmacies or drug stores employ Pharmacists to fill prescriptions with the prescribed amount of a prescribed medicine or dose. The Pharmacist fills the prescription from a bulk package of medicine into a delivery package sized for the consumer. Although Pharmacists are very careful to dispense the correct quantity of the correct medicine, ever too often, the wrong quantity is dispensed, or worse yet, the wrong medicine is dispensed.

The medicine is often delivered to the consumer in a package that is a container with a lid, for example, a vial or bottle. After counting the prescribed amount of medicine, the Pharmacist funnels the pills into the container, attaches the lid and places a label on the container indicating what medicine is stored inside and information related to the medicine. Again, the transfer of pills into the container creates another opportunity for one or more pills to be lost, thereby not providing the proper amount to the consumer.

With some consumers, it may be difficult to remember which pill to take, when to take it, and even whether they have already taken the pill. To overcome this problem, an array pack was devised with a series of compartment resembling cups or blisters, each "blister" containing one or more pills that are to be taken at the same time. This form of packaging is known as "blister packs," "dose packs," "bingo cards," and "punch cards." Often, cold medicine is supplied to consumers on such a card with a single dose in each blister and then the blister pack is packaged in a simple box with labels and advertising on the outside. Although a huge benefit to the consumer, filling the blister pack with a prescription involves the Pharmacist sitting down and laboriously dispensing the doses by hand into the individual blisters of the pack, then sealing the back. Furthermore, for prescriptions in which the dosage varies by day, extra attention to detail is required because each blister may have different quantities of pills or pills of a different strength or a combination of such, again feeding into the probability of error.

Presently, automation equipment is available for automatically filling prescriptions from a plurality of pill storage bins (or canisters). Each storage bin is filled with a supply of a given medicine in pill, capsule or gel-cap form. The storage bin has an electro-mechanical dispensing control and the dispensing control is controlled by a machine control that has, for example, a user interface for the Pharmacist to enter the medicine name, strength and quantity, thereby initiating the dispensing of that number of pills. The pills are then directed into a vial.

The art of filling containers with pills is quite old, going back to U.S. Pat. No. 2,457,220 to Fowler, et al issued Dec. 28, 1948; which is hereby incorporated by reference and describes a motorized pill dispensing machine. This machine has one storage area for a supply of pills that are thereafter handled by the machine in groups of a known quantity. As the machine rotates, the pills fall into receptacles numbering that known quantity, then as it further rotates, that number of pills falls through an opening, into a funnel and then into a pill container in the shape of a bottle or vial. This device is limited to dispensing a fixed quantity of a single type of pills into bottles.

U.S. Pat. No. 6,318,051 B1 to Preiss, issued Nov. 20, 2001; which is hereby incorporated by reference describes a device for dispatching singular items from a single supply station into product packs (blister packs) of the same type and is useful in an assembly line process of filling blister packs with a single medication. This device is limited to dispensing a single type of pill into a single type of blister pack. Likewise, U.S. Pat. No. 6,805,259 B2 to Stevens, et al, issued Oct. 19, 2004; hereby incorporated by reference, also describes a tablet dispenser that dispenses tablets from multiple reservoirs into blister packs. Although not limited to one medication as the previous patents, this device is limited to dispensing only into blister packs.

U.S. Pat. No. 6,925,774 B2 to Peterson, issued Aug. 9, 2005 is hereby incorporated by reference. It describes a machine a machine for filling blister package cavities. This device does not fill vials and to do so, a pharmacy would need to purchase a second machine.

U.S. Pat. No. 7,006,894 to de la Huerge, issued Feb. 28, 2006 is hereby incorporated by reference. This patent describes a device for filling a medication cassette which is then provided to a patient in a hospital setting. The disclosed device does not fill vials and/or blister packs from a plurality of canisters.

Unfortunately, the prior art does not provide the flexibility of interchangeable platens wherein multiple platens are provided for a single dispensing device and each platen has a identifier used by the dispensing device to determine the configuration of an installed platen.

What is needed is a method and apparatus that will accurately fill a prescription from a plurality of canisters into a target package wherein the target package is held by a platen or a plurality of platens, each platen adapted to easily install into the apparatus and each platen having a and writable embedded device.

SUMMARY

An objective of the invention is to provide an apparatus for dispensing pills, the apparatus having a plurality of interchangeable platens, each platen adapted to hold either a vial or any one of a plurality of blister package types. Each platen has a writable platen identifier.

Another objective of the present invention is to provide an apparatus for dispensing pills, the apparatus having at least two platens, a first of the at least two platens adapted to hold a vial and a second of the at least two platens adapted to hold a particular blister pack, whereas the at least two platens are installable into the apparatus without the use of tools.

Another objective of the present invention is to provide an apparatus for dispensing pills, the apparatus having at least two platens and each platen having a platen identifier.

In one embodiment, a device for dispensing pills is disclosed including a set of pill canisters each containing pills. The device for dispensing pills has a plurality of platens, each of the platens being substantially planar and each having a platen identifier. Each of the platens has pill locations corresponding to one of more specific packaging configurations. There is a selected platen from the plurality of platens that removably holds and supports a target container. The device for dispensing pills has a frame that is situated beneath the target location. The selected platen is removably and interchangeably held in the frame and the selected platen moves in both an X axis and/or a Y axis responsive to movement of the frame in both the X axis and/or the Y axis. The device for dispensing pills has a device for communicating with the platen identifier and a control that accesses the device for communicating with the platen identifier and obtains data from the platen identifier. The control moves the selected platen in the X axis and/or the Y axis responsive to the data and releases a desired quantity of the pills at a target location into the a target package that is held by the selected platen.

In another embodiment, a method for dispensing pills is disclosed including providing a device for dispensing pills having a plurality of pill canisters. Each of the pill canisters contains pills. The device for dispensing pills has a plurality of platens. Each of the platens is substantially planar and has a platen identifier. Each of the platens has pill locations corresponding to one of more specific packaging configurations. The device for dispensing pills includes a frame situated beneath the target location. Any of the platens is removably and interchangeably held in the frame and the frame moves in both an X axis and/or a Y axis responsive to a control. A device for communicating with the platen identifier is interfaced to the control. The method includes a first target package to be filled and a first platen from the plurality of platens is selected and the first target package is placed into the first platen. The first platen is configured to hold and support the first target package. The first platen is inserted into the frame and the control reads data from the platen identifier and uses the data to move the frame and first platen in the x-axis and/or the y-axis and dispense pills into the first target package in x-axis and y-axis locations as determined by the data. After the pills are dispensed, the first platen is removed from the frame and the first target package is removed from the first platen. Now a second target package is to be filled and a second platen from the plurality of platens is selected and the second target package is placed into the second platen. The second platen is configured to hold and support the second target package. The second platen is inserted into the frame and the control reads data from the platen identifier and uses the data to move the frame and second platen in the x-axis and/or the y-axis and dispense pills into the second target package in x-axis and/or y-axis locations as determined by the data. After the pills are dispensed, the second platen is removed from the frame and the second target package is removed from the second platen.

In another embodiment, a device for dispensing pills is disclosed. The device has a plurality of pill canisters, each containing a quantity of pills and a controller. The device also has a way to select a source pill canister from the plurality of pill canisters by direction of the controller and a way to release a desired quantity of the pills from the source pill canister also by direction of the controller. The desired quantity of pills is released at a target location. The device has a plurality of platens, each having a platen identification. An active platen that is selected from the plurality of platens is held in a frame and the frame moves the active platen in both an X axis and/or a Y axis by direction of the controller, positioning the active platen beneath the target location. The active platen is removably held by the frame. A device for interfacing with the platen identification is communicatively connected to the controller.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION

Figure 1:
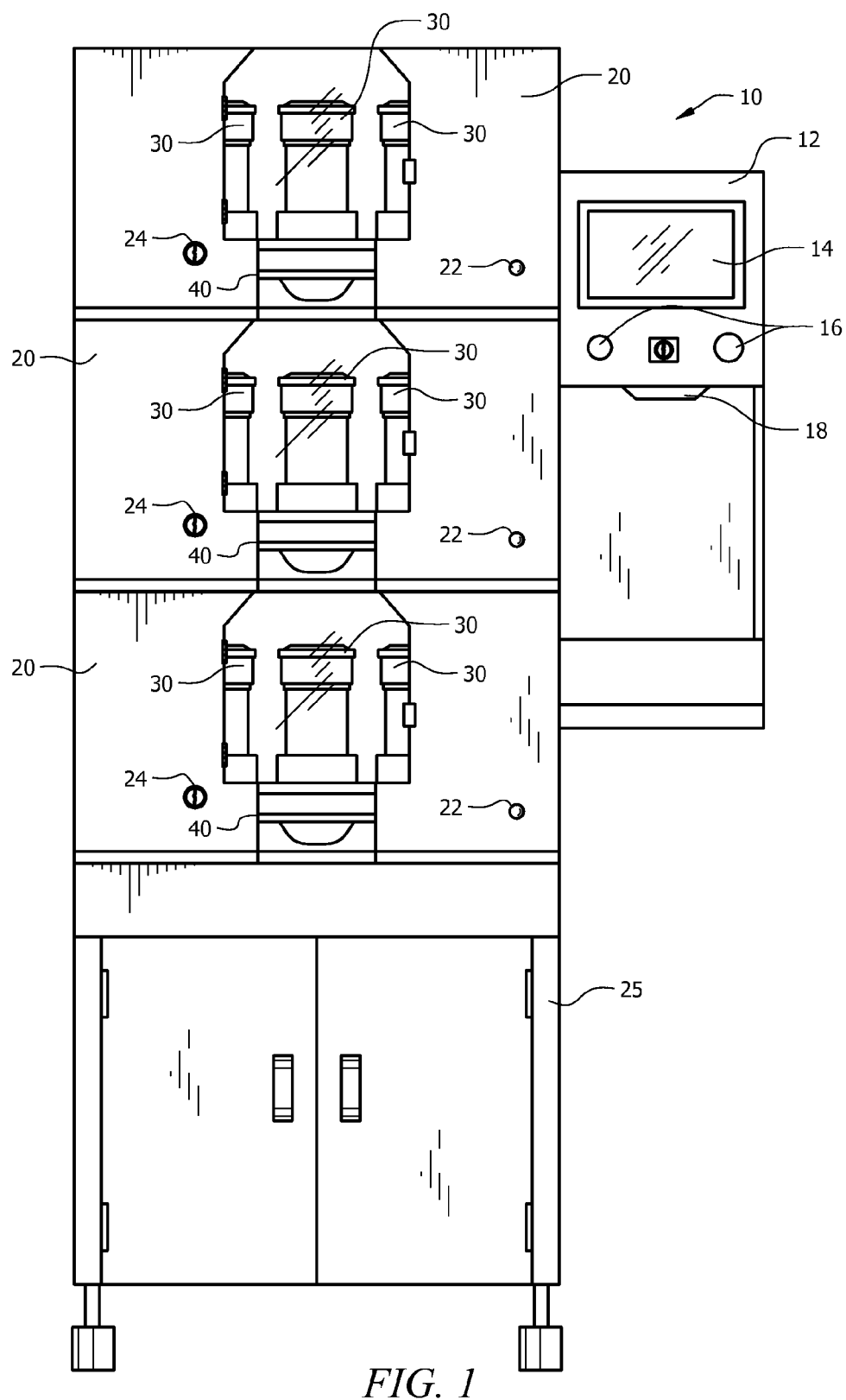
FIG. 1 illustrates a plan view of a pill dispensing machine.

Reference will now be made in detail to the presently preferred embodiments of the invention, examples of which are illustrated in the accompanying drawings. Throughout the following detailed description, the same reference numerals refer to the same elements in all figures. Throughout the description (including the claims), the word "pill" is used generically. For the purpose of this application, the word pill is used to represent anything that can be dispensed by the device of the present invention and there is no limitation placed upon that which is dispensed. For example, tablets, capsules, caplets and gel-caps can be dispensed as well as coated candy (e.g., placebos). The present invention works well with most any solid object and can be scaled to work for much larger objects as well. Throughout the description (including the claims) the forms of packaging are referred to as vials or blister packs. For the purpose of this application, the word vial is used to represent any container having a single compartment for storing pills including, but not limited to, vials, bottles, tubes and the like. Often, these vials are configured to accept a lid that either snaps in place or screws in place. Blister packs refer to a class of packaging that has multiple compartments, wherein each compartment optionally (it is possible for some compartments to be empty) stores a dose of one or more pills, either the same pills or different pills. Other names for blister packs are, for example, dose packs, bingo cards and punch cards. The individual blisters of the blister pack can be arranged in any fashion, such as a linear series of blisters and a matrix of blisters and may be evenly spaced or not. Often, blister packs are sealed by a thin sheet that adheres to their open side, allowing one blister at a time to be pierced to gain access to the pills within that blister.

Throughout this description, the term canister refers to a dispenser or canister for a single pill type. The canister has a storage compartment for the pills and a mechanism for dispensing an accurate count of the pills. Canisters are sometimes referred to in the industry as cassettes or other names.

Referring to FIG. 1, a plan view of a pill dispensing machine of the present invention is shown. The pill dispensing machine 10 has a control station 12 and three dispensing stations 20, although any number of dispensing stations is anticipated. The control station 12 has a display 14 and input device/controls 16. In some embodiments, the control station 12 has a bar code scanner 18. In such embodiments, the request (e.g., pill type and desired quantity) is scanned from a label on the target package.

Each dispensing station 20 is shown with a removable platen 40 installed into which a vial or blister pack is inserted for the automated dispensing of pills. Visible through a window are a plurality of pill canisters 30, each pill canister 30 containing a plurality of pills of a particular type. The pill canisters 30 are adapted to a carousel or other selection device (e.g., robotic arm, linear row of canisters, etc). In the shown embodiment, a number of canisters 30 are adapted to a carousel (not visible). Since there are multiple dispensing stations 20, each dispensing station has an indicator 22 and a lock 24. The lock 24 reduces the threat of unauthorized access to pills held in the canisters. The indicator 22 informs the operator which of the dispensing stations will be used to fill a prescription. As an example, the operator (e.g., pharmacist) enters the request (e.g., prescription information) at the control station 12 either by data entry or by scanning a bar code or similar identifier. Once the control station 12 determines which canister holds the pill type required for the prescription, the indicator 22 illuminates on the dispensing station 20 having the correct pill type telling the operator where to place the target package (e.g., blister pack or vial) for filling the prescription. In some embodiments, the dispensing stations 20 are supported by a cabinet 25 or other support structure as known in the industry.

Figure 2:
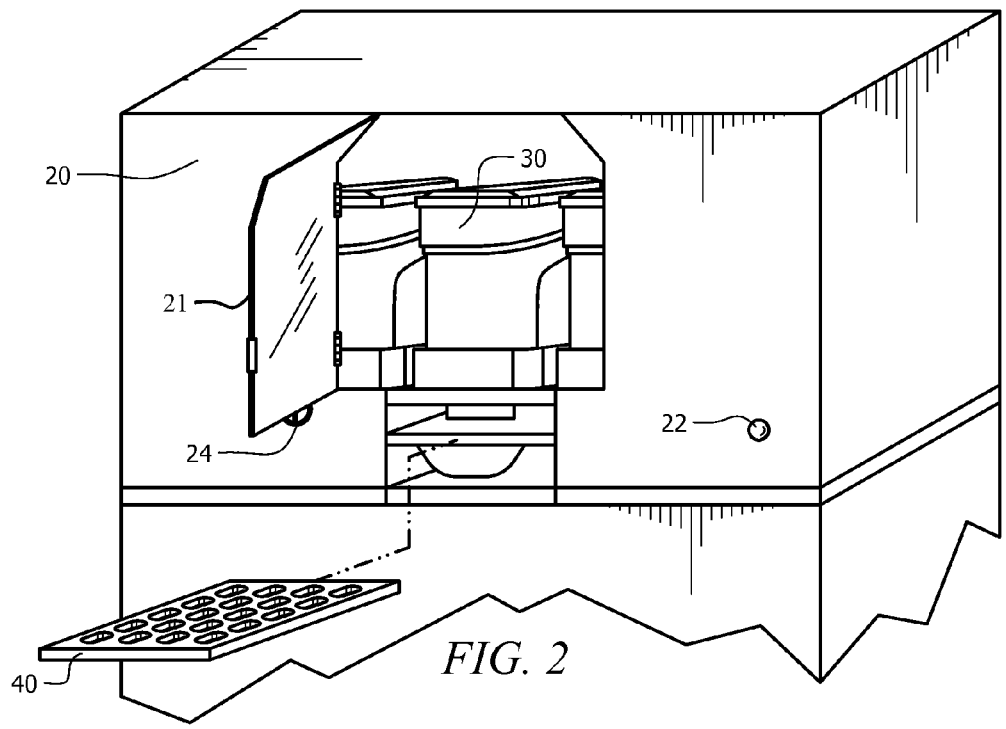
FIG. 2 illustrates a perspective view of an individual pill dispensing device.

Referring to FIG. 2, a perspective view of an individual pill dispensing station 20 of the present invention is shown with its door 21 open. The dispensing station 20 is shown with a door 21 in the open position showing the canisters 30. The lock 24 is partially visible as well as the indicator 22. One particular platen 40 for dispensing pills into a particular blister pack (not shown) is shown installed in the dispensing station 20. Before dispensing pills, the platen 40 is inserted into a frame 250 (see FIGS. 8A, 8B, 9) of the dispensing station 20. Although a particular platen 40 is shown, many configurations of platens 40/44/48, etc., are anticipated. Of the various individual platens 40/44/48, each platen is adapted to hold and support one or more particular blister packs or one or more vials (bottles, etc).

Figure 3:
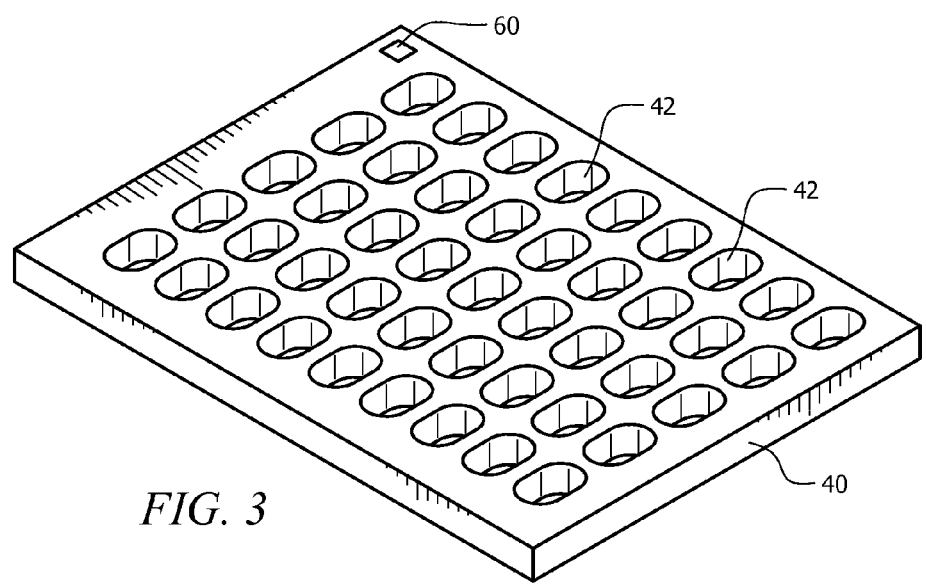
FIG. 3 illustrates a perspective view of a first exemplary platen for holding a particular type of blister package.

Referring to FIG. 3, a perspective view of a first exemplary platen for holding a particular type of blister package of the present invention is shown. This particular platen 40 is configured to hold one or more specific blister packs having a certain number of blisters of one or more blister sizes. For example, the platen 40 shown has cavities 42 for accepting the blisters of several different blister packs. The platen 40 supports blister packs having a similar spacing and sizing of blisters having a configuration up to 5×9 blisters. For example, one such blister pack has 1×7 blisters while another such blister pack has 5×8 blisters, etc. If the blisters of a certain blister pack are not spaced similar to the platen 40 or the blisters are too big to fit within the cavities 42, another platen is needed to support that particular blister pack.

Also visible in FIG. 3 is an identification device 60. The identification device 60 is read by the dispensing station 20 when the platen 40 is inserted into the dispensing station 20 (as will be shown in subsequent figures). In some embodiments, the identification device 60 is an RFID (radio frequency identification device) 60 and the dispensing station 20 includes electronics to read the value/data stored in the RFID 60. In some embodiments, the identification device 60 is a bar code 60 and the dispensing station 20 includes a scanner to read the bar code 60 when the platen 40 with the bar code is inserted into the dispensing station 20. In some embodiments, the identification device 60 is a magnetic stripe 60 (e.g., as used on credit cards) and the dispensing station 20 includes electronics to read the value/data stored in the magnetic stripe 60. In other embodiments, any other known identification device and sensing device known is included here within.

Figure 4:
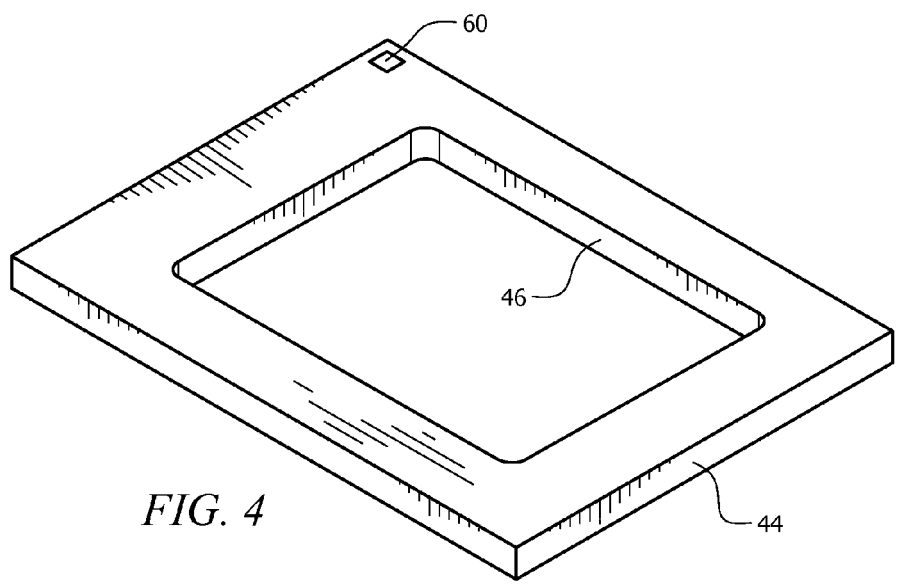
FIG. 4 illustrates a perspective view of a second exemplary platen for holding a particular type of blister package.

Referring to FIG. 4, a perspective view of a second exemplary platen for holding a particular type or class of blister packages of the present invention is shown. This particular platen 44 is configured to hold one or more specific blister packs having a certain outer dimension. For example, the platen 44 shown has a rectangular opening 46 for holding and supporting blister packs having a rectangular outer shape of a similar size (height/width). It is anticipated that the opening 46 is of any shape needed to match a particular blister pack such as rectangular, square, round, etc.

Also visible in FIG. 4 is an identification device 60. The identification device 60 is read by the dispensing station 20 when the platen 40 is inserted into the dispensing station 20 (as will be shown in subsequent figures). In some embodiments, the identification device 60 is an RFID (radio frequency identification device) 60 and the dispensing station 20 includes electronics to read the value/data stored in the RFID 60. In some embodiments, the identification device 60 is a bar code 60 and the dispensing station 20 includes a scanner to read the bar code 60 when the platen 40 with the bar code is inserted into the dispensing station 20. In some embodiments, the identification device 60 is a magnetic stripe 60 (e.g., as used on credit cards) and the dispensing station 20 includes electronics to read the value/data stored in the magnetic stripe 60. In other embodiments, any other known identification device and sensing device known is included here within. As described in FIG. 8A, in some embodiments, the identification device 60 is also writable, for example an RFID with writable memory. Although there are many anticipated uses for having a platen identification device 60 that is writable, one typical scenario includes loading a platen with a package (vial or blister pack) and writing to the identification device 60 a prescription (e.g. pill types, quantities, pack coordinates). In this way, when the preconfigured platen 40/44/48/41 (see FIGS. 5, 8A, 8B) is placed in the frame, the dispensing station 20 reads the prescription from the identification device 60 and properly dispensed the pills into the blister pack 70.

In some embodiment, the platen 40/44 have bottom arrangements and the platen 40/44 itself is adapted to receive and accept pills at the target location. In such, the platen 40/44 is filled with the desired pills, then the platen is removed from the pill dispensing station 20 and the pills are then transferred to a target container.

Figure 5:
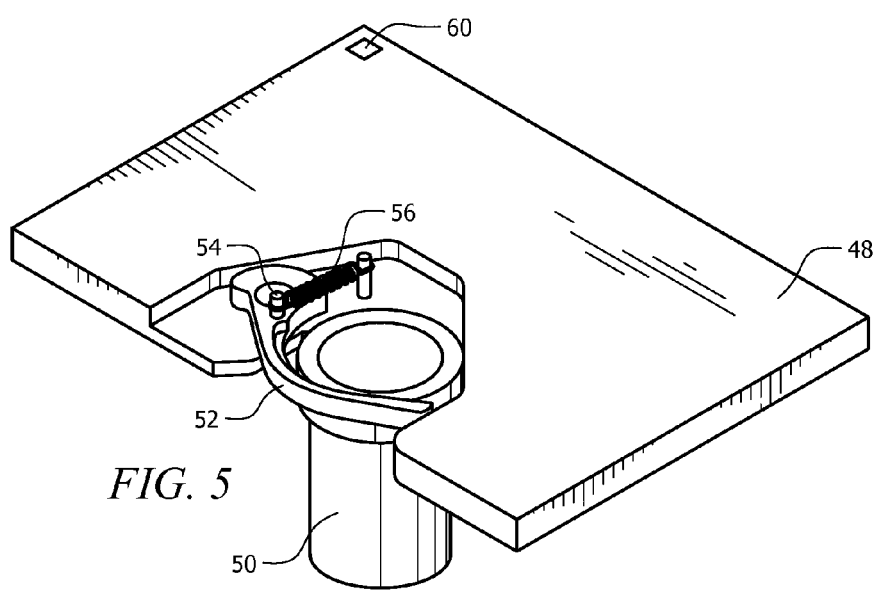
FIG. 5 illustrates a perspective view of a third exemplary platen for holding a vial package of the present invention.

Referring to FIG. 5, a perspective view of a third exemplary platen for holding a vial of the present invention is shown. This particular platen 48 is configured to hold one of various pill bottles or vials 50. The platen 48 includes an arm 52 that is pivotally attached to the platen 48 by a pin 54 or other pivot device as known in the industry. The arm 52 is urged closed by a spring 56, thereby holding the bottle or vial 50 against the platen 48. As shown the arm 52 holds vials 50 of varying diameters, shapes and heights.

Also visible in FIG. 5 is an identification device 60. The identification device 60 is read by the dispensing station 20 when the platen 40 is inserted into the dispensing station 20 (as will be shown in subsequent figures). In some embodiments, the identification device 60 is an RFID (radio frequency identification device) 60 and the dispensing station 20 includes electronics to read the value/data stored in the RFID 60. In some embodiments, the identification device 60 is a bar code 60 and the dispensing station 20 includes a scanner to read the bar code 60 when the platen 40 with the bar code is inserted into the dispensing station 20. In some embodiments, the identification device 60 is a magnetic stripe 60 (e.g., as used on credit cards) and the dispensing station 20 includes electronics to read the value/data stored in the magnetic stripe 60. In other embodiments, any other known identification device and sensing device known is included here within. As described in FIG. 8A, in some embodiments, the identification device 60 is also writable, for example an RFID with writable memory.

Figure 6:
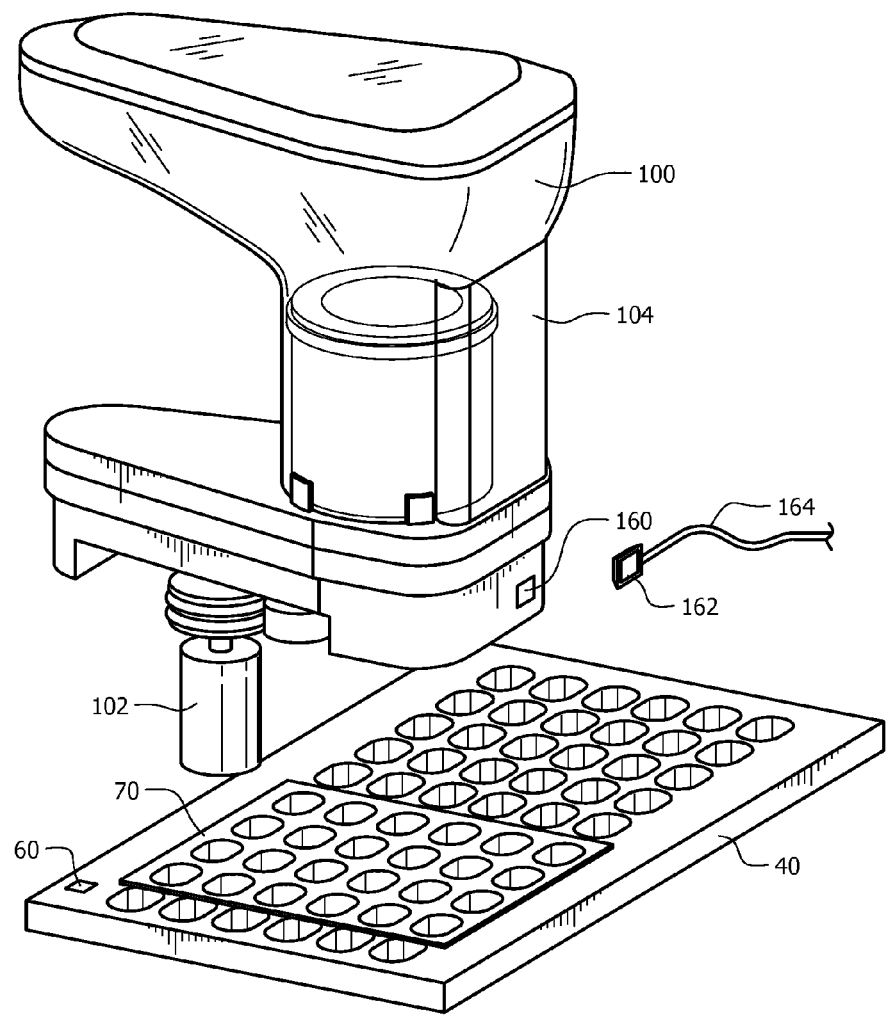
FIG. 6 illustrates a perspective view of a pill dispensing device with the first platen installed beneath the active dispensing canister.

Referring to FIG. 6, a perspective view of a pill dispensing station with the first platen installed beneath the active dispensing canister is shown. In this view, the cabinetry, carousel and drive mechanisms are left out to highlight certain aspects of the present invention. A pill canister 100 is positioned over a target location (the location to which pills are dropped from the pill canister 100). In some embodiments, the pill canister has a label 104 to inform the user (e.g., pharmacist) what type of pill the canister 100 holds.

In some embodiments, a canister identification 160 is present on the body of the canister (any convenient location on the canister). The identification 160 is electronically read by the dispensing station 20 to determine which pill type is loaded in individual locations about the dispensing station (e.g., different locations on the carousel). In some embodiments, the identification 160 is a bar code or other optically readable media. In such, an optical reader 162 is used by the dispensing station to read the bar code 160 and determine the pill type contained in the canister 100. The optical reader 162 is connected to the dispensing station 20 by wires 164. In some embodiments, the identification is a RFID tag (radio frequency identification tag) 160 and the RFID tag 160 is read by a RFID reader/writer 162. The RFID reader 162 is connected to the dispensing station 20 by wires 164. In some embodiments having a RFID identification device 160, the RFID tag 160 is read-only. In other embodiments having a RFID identification device 160, the RFID tag 160 has some read-only data and some read/write data. The read/write data is used for various features/functions such as writing a pill count to the RFID identification 160 before removing the canister 100 from the dispensing station 20. In this way, an initial pill count is written to the RFID identification 160 when the canister 20 is initially filled, then when pills are dispensed, the count is decremented such that the RFID identification 160 always contains an accurate count of the pill count within the canister 100. This is useful when there are more pill types than positions in the dispensing stations 20 and certain canisters 20 with certain pill types are swapped between the dispensing station 20 and a storage location (not shown).

Also shown in FIG. 6 is a platen 40 for holding blister packs such as the 4×6 blister pack 70 shown. It should be noted that the platen 40 is capable of holding a variety of blister pack configurations such as the 4×6 blister pack 70 shown as long as the blister spacing is similar to that of the platen 40 and the total blister locations horizontally and vertically do not exceed the blisters on the platen 40. In such cases, a different platen is required having the correct configuration for the desired blister pack. The platen 40 has a platen identification 60. The platen identification 60 is, in some embodiments, an optically scannable device (e.g., bar code) and in other embodiments an RFID as previously described. The platen identification 60 is used by the dispensing station 20 to determine which platen is present in the dispensing station 20 as will be shown. As described in FIG. 8A, in some embodiments, the identification device 60 is also writable, for example an RFID with writable memory.

For completeness, a canister drive motor 102 is shown. The internal operation of the canister 20 is shown, for example, in the cited references as well as other such devices are known in the industry.

Figure 7:
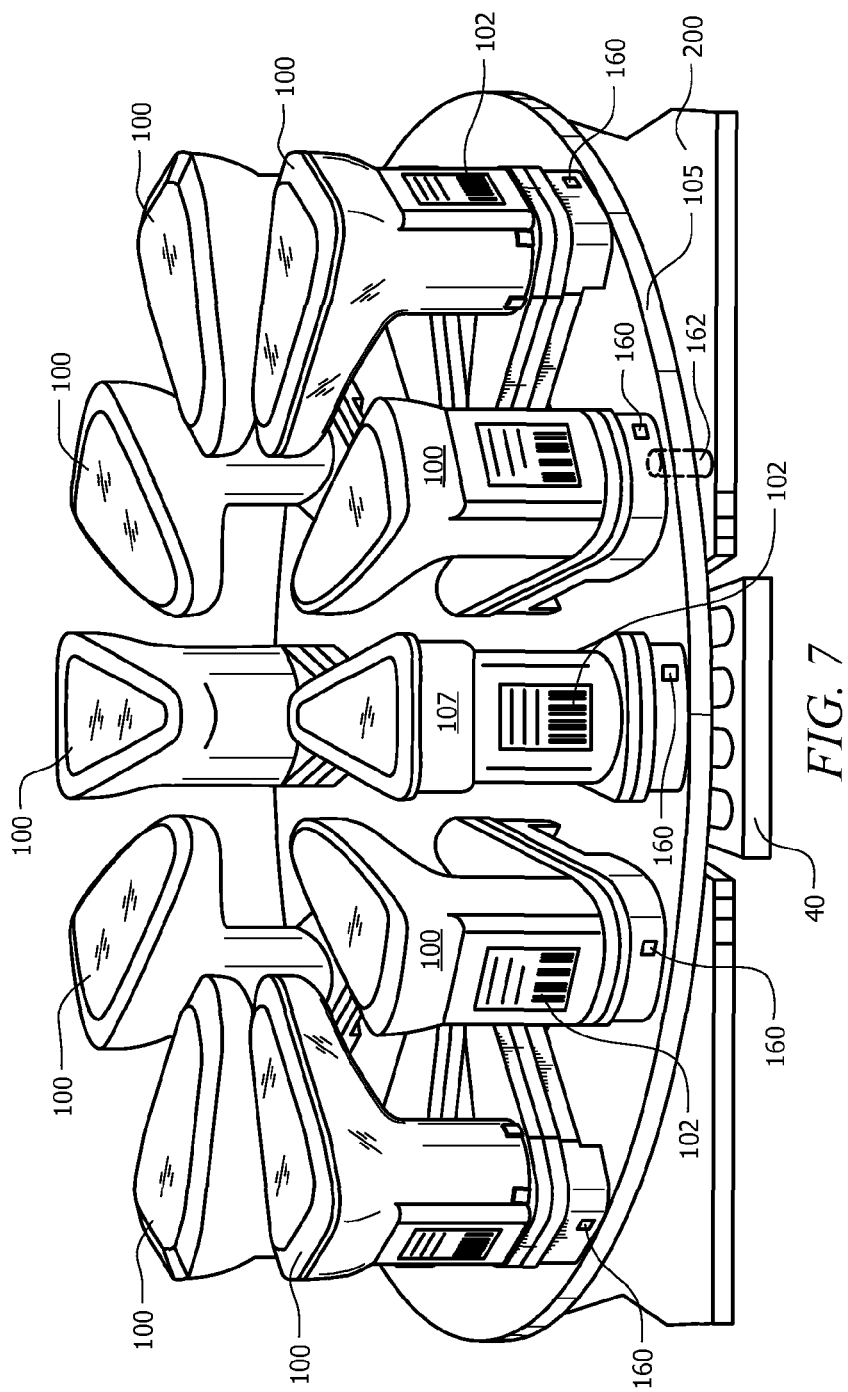
FIG. 7 illustrates a perspective view of a pill dispensing device with a fourth platen installed beneath the active dispensing canister, showing 10 canisters adapted to a carousel.

Referring to FIG. 7, a perspective view of a pill dispensing device with a platen 40 installed beneath the active dispensing canister 107, showing ten canisters 100/107 adapted to a carousel 105 is shown. In this example, ten canisters 100 are mounted housed on a carousel 105 and the carousel 105 rotates to position the desired canister 107 over the target location of the installed platen 40. Any number of canisters 100/107 are anticipated as well as other methods known in the industry to select a particular canister 107 and move that canister 107 to the target location including, but not limited to, robotic arms, a linear row of canisters 100/107 movable in one plane (e.g., left and right). Also shown in this example is the platen 40 positioning table 200 which positions the platen 40 beneath the target location, moving the platen 40 in an X and/or Y direction as needed to fill either vials or blister packs. Details of one specific positioning table are described with FIGS. 8A, 8B and 9.

Also, in this example, each canister has a canister identification device 160 and the dispensing machine has a reader 162 for reading the canister identification device 160 and determining which canister 100 is in each possible position. In some embodiments, the canister identification device 160 is a bar code and the reader 162 is a bar code reader. In some embodiments, the canister identification device 160 is an RFID and the reader 162 is a RFID reader.

In some embodiments, the canister identification device 160 is an RFID with writable storage and the reader 162 is an RFID reader/writer. In such embodiments, various data is written to the RFID by the dispensing station 20. For example, a quantity field within the read/write data area of the RFID is reserved for a quantity of pills present in the canister 107. When the canister 107 is filled at a filling station, the quantity field in the RFID 160 is set to the number of pills in the canister 107. During dispensing, the quantity of pills in the canister 107 is read from the quantity field of the RFID 160 to determine if sufficient pills are present in the canister 107. After dispensing a quantity of pills, the new quantity of pills present in the canister 107 is written back to the RFID 160 so that, if the canister is moved, etc., the RFID 160 will contain an accurate count of pills within the canister 107.

Figure 8A:
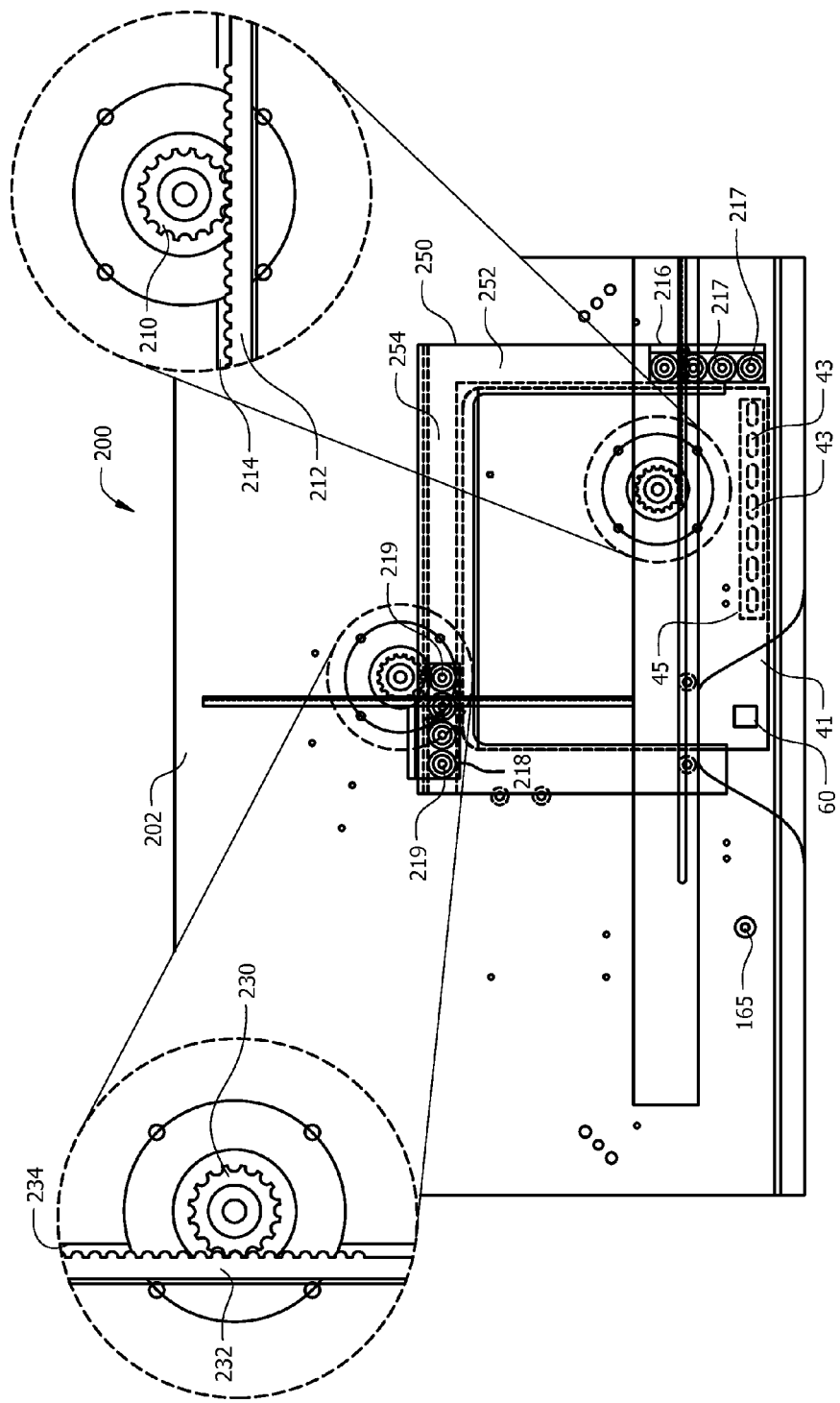
FIG. 8A illustrates a plan view of an X-Y transport.
Figure 8B:
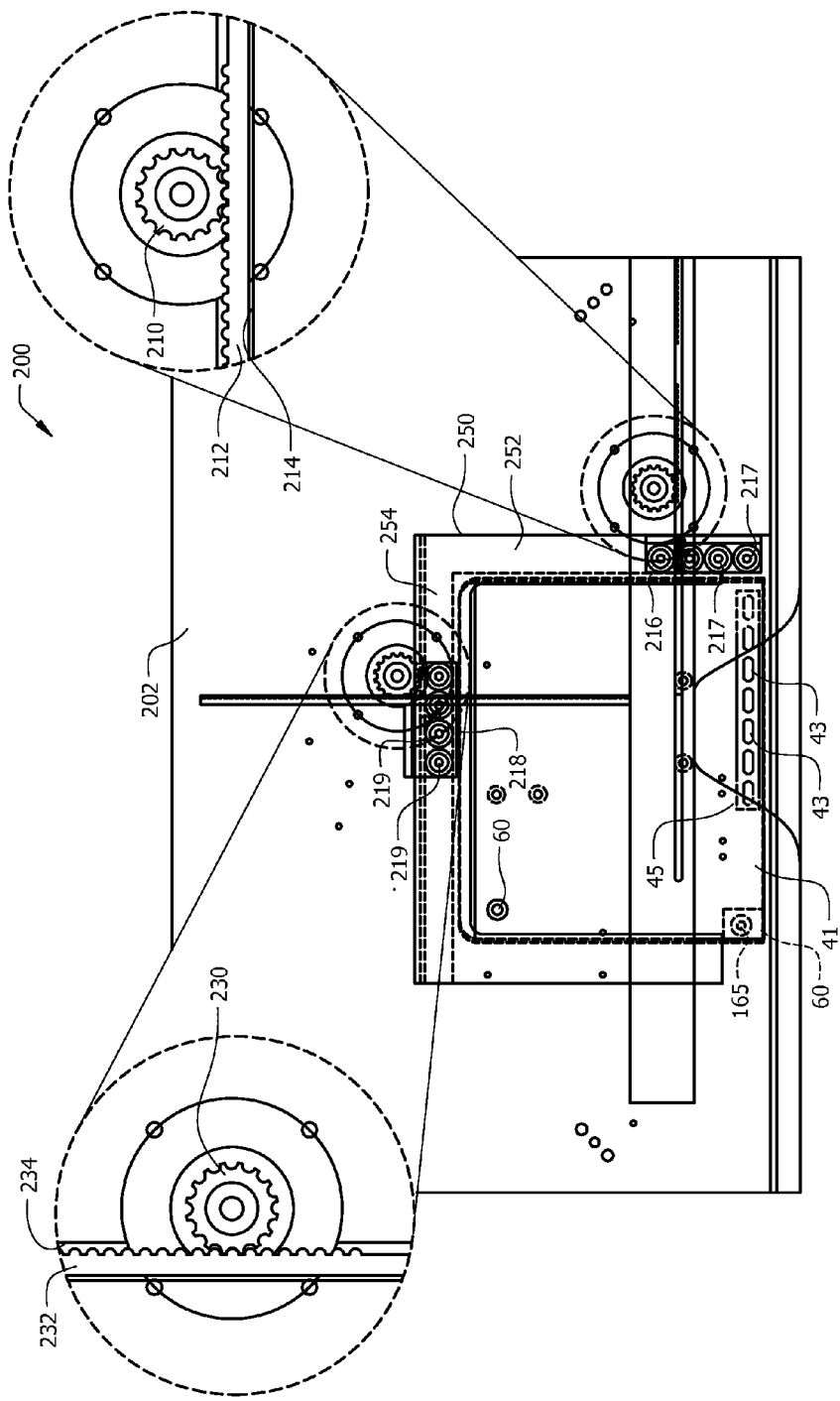
FIG. 8B illustrates a plan view of a second positioning of the X-Y transport.
Figure 9:
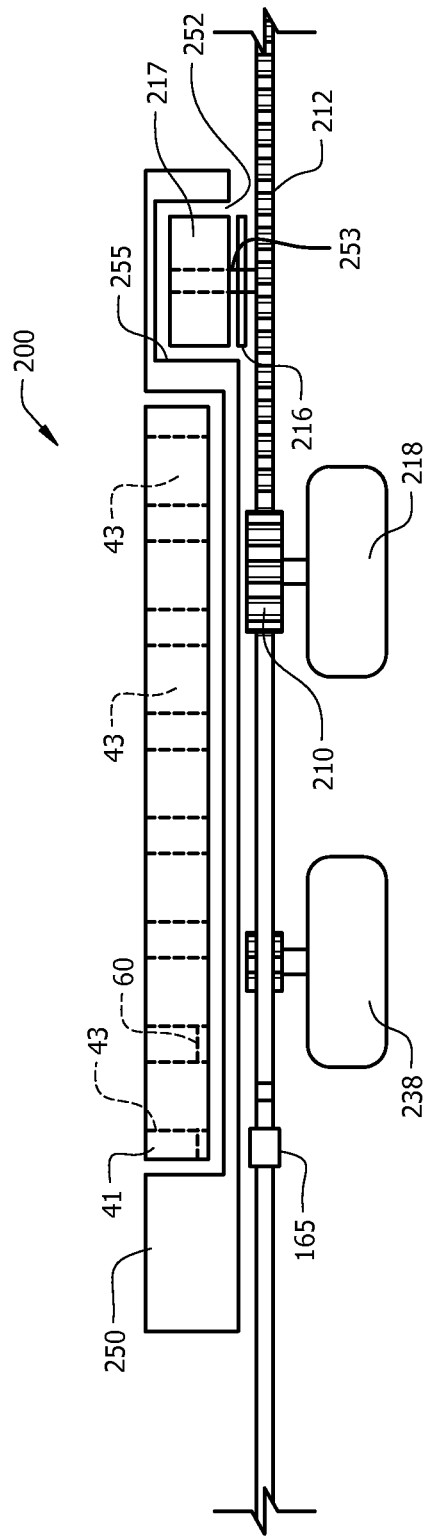
FIG. 9 illustrates a side cross-sectional view of the X-Y transport.

Referring to FIG. 8A, a plan view of an X-Y positioning table 200 of the present invention is shown. Although there are many ways known in the industry to position a platen 41 beneath a target location such as those described in the referenced patents and all of which are included here within, the X-Y positioning table 200 of FIGS. 8A, 8B and 9 provide a unique, low-profile positioning table. The X-Y positioning table 200 includes a stationary base 202 and a frame 250 that is movable in both the X direction and the Y direction. In the present invention, one of the possible platens such as a platen 41 configured to hold a blister pack 45 having seven compartments 43 is inserted into the frame 250 and the X-Y positioning table 200 positions the desired compartment 43 beneath the target location.

The X-Y positioning table 200 has two positioning drive motors or servo motors 218/238 (see FIG. 9) mounted to the stationary base 202. Each of the positioning drive motors or servo motors 218/238 is interfaced to drive gears 210/230. The X drive gear 210 interfaces to an X-plane linear gear 212 and the Y drive gear 230 interfaces to a Y-plane linear gear 232. Rotation of either of the drive gears 210/230 results in linear movement of the respective linear gear 212/232. The X-plane linear gear 212 is held within an X-direction slot 214 while the Y-plane linear gear 232 is held within a Y-direction slot 234, each slot 214/234 maintains directionality and holds the linear gears 212/232 in relation to the drive gears 210/230.

The X-plane linear gear 212 is affixed to an X-plane truck 216. Movement of the X-plane truck 216 in response to rotation of the X-plane linear gear 212 results in movement of the frame 250 in the X direction. The X-plane truck 216 has bearings 217 that travel within an X-truck trough 252 of the frame 250. Likewise, the Y-plane linear gear 232 is affixed to a Y-plane truck 218. Movement of the Y-plane truck 218 in response to rotation of the Y-plane linear gear 232 results in movement of the frame 250 in the Y direction. The Y-plane truck 218 has bearings 219 that travel within a Y-truck trough 254 of a frame 250. In this way, as the X-plane linear gear 212 moves in the X direction, the Y-plane truck 218 travels within the Y-truck trough 254. As the Y-plane linear gear 232 moves the frame 250 in the Y direction, the X-plane truck 216 travels within the X-truck trough 252. In this way, the frame 250 moves in both the X direction and the Y direction with respect to the base table 202 responsive to rotation of the X drive gear and rotation of the Y drive gear. Since there is no required overlap of the X-drive and Y-drive mechanisms, the X-Y table of the present invention requires less z-axis thickness.

Although the frame 250 is movable in both the X-axis and the Y-axis, it is anticipated that, for certain platens 40/41/44/48, the frame 250 is moved in only one of the X-axis and Y-axis, for example, when there is a single row or column of pill locations, etc.

In some embodiments, each platen [41] includes a platen identification 60. In some embodiments, the platen identification 60 is a bar code. In some embodiments, the platen identification 60 is an RFID. In some embodiments, the platen identification 60 has writable data storage such as a writeable RFID. In other embodiments, the platen identification 60 is any known identification device known in the industry. A platen identification reader 165 for reading the platen identification 60 (e.g., a bar code reader or an RFID reader) is provided within the dispensing station 20. In some embodiments in which the platen identification 60 has writable data storage (e.g., writeable RFID), the platen identification reader 165 is adapted to write data to the platen identification 60.

In embodiments in which the platen identification 60 has writable data storage (e.g., writeable RFID); information is written to the platen identification 60 and read/used at a later time. For example, the request (e.g., pill type, pill quantity, distribution in blister pack, etc.) is written to the platen identification 60 externally to the dispensing station 20 then when the platen [41] is inserted into the dispensing station 20, the request is read from the platen identification 60. In some embodiments, after filling the request, the request is then overwritten or cleared by the dispensing station 20 so the same request is not later duplicated.

Referring to FIG. 8B, a plan view of a second positioning of the X-Y transport of the present invention is shown. This view shows the frame 250 and platen 41 have moved left (X-direction) with respect to the position of the frame 250 in FIG. 8A. To get to this position, the X-plane drive gear 210 rotated clockwise resulting in the X-plane linear gear 212 moving left (X-direction) within the X-slot 214. As the frame 250 and platen 41 move left, the bearings 219 of the Y-truck 218 move within the Y trough 254. Note that in FIG. 8B, the platen identification 60 is over the reader 165.

Referring to FIG. 9, a side cross-sectional view of the X-Y transport 200 of the present invention is shown. In this, the platen 41 is held within the frame 250. The X-drive motor/servo 218 interfaces with the X-drive gear 210 and the X-drive gear 210 meshes with the X-plane linear gear 212. The Y-drive motor/servo 238 is visible. The X-plane linear gear 212 interfaces to the X-plane truck 216 by a post 253. One or more bearings 217 are mounted to the X-plane truck and the bearings are slideably interfaced to the X-truck trough 252 formed in the frame 250. Note that it is preferred that the bearings 217/219 be ball bearings. In some embodiments, the bearings 217/219 are brass or nylon bearings. In some embodiments, the bearings 217/219 are a solid, non-rotating object that slides down the truck troughs 252/254. In some embodiments, the truck troughs 252/254 have flat edges 255 while in other embodiments, the truck troughs 252/254 have flared edges or lipped edges to hold the bearings 217/219 within the truck troughs 252/254.

Figure 10:
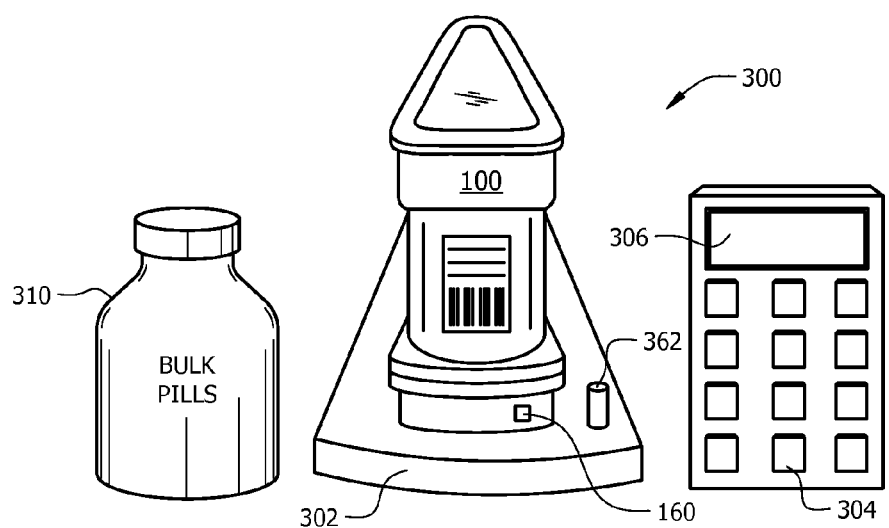
FIG. 10 illustrates a canister loading station.

Referring now to FIG. 10, a canister loading station of the present invention is shown. The canister loading station 300 has a stand or platform 302 adapted to securely hold a canister 100. Bulk pills are provided in a bulk pill container 310. Pills from the bulk pill container 310 are counted and placed into the canister 100. In some embodiments, the canister loading station 300 includes an input device such as a keypad 304 or touch screen (not shown). In some embodiments, the canister loading station 300 includes a display 306. In embodiments having a display 306, the canister identification 160 is read by a canister loading station reader 362 and the proper pill type is displayed on the display 306. In embodiments having both a display 306 and input device 304, the canister identification 160 is read by a canister loading station reader/writer 362 and the proper pill type is displayed on the display 306 and, after loading the quantity of pills into the canister, the user enters that quantity at the input device 304 and the canister loading station reader/writer 362 writes the quantity of pills present in the canister 100 into the canister identification 160.

Figure 11:
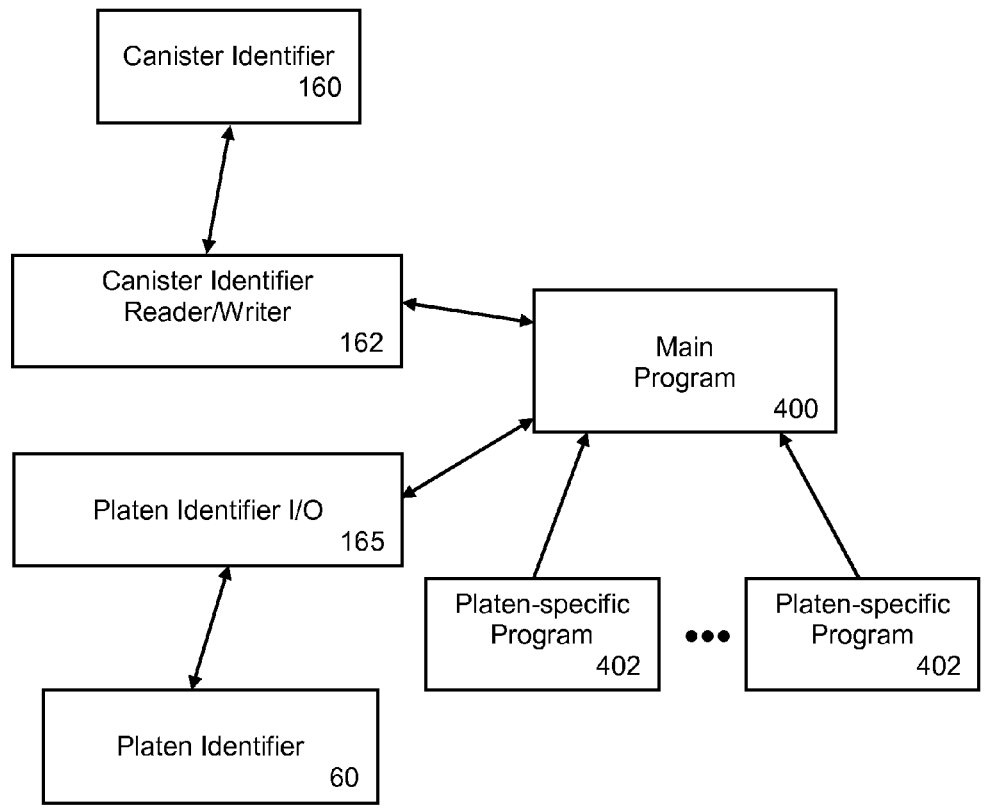
FIG. 11 illustrates a block diagram of the dispensing station.

Referring to FIG. 11, a block diagram of the dispensing station of the present invention is shown. Information from the canister identifier 160 (on a canister 100) is read by the canister identifier reader/writer 162 and the information is provided to the main program 400 running on the controller 500 (see FIG. 12). In some embodiments in which the canister identifier is writable, information such as an updated pill count is sent from the main program 400 to the canister identifier reader/writer 162 and, the canister identifier reader/writer 162 writes the information to the canister identifier 160.

Figure 12:
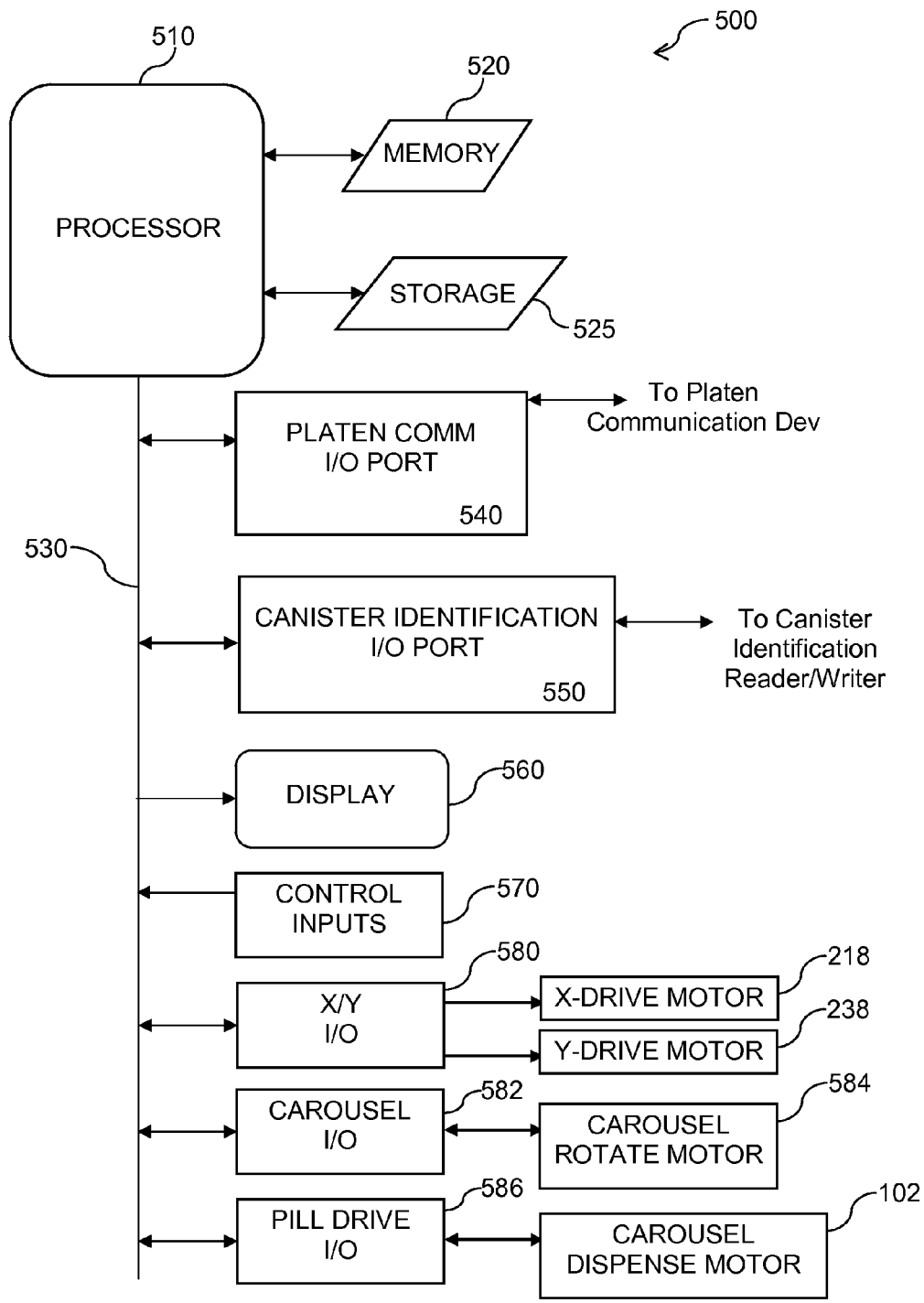
FIG. 12 illustrates a controller of the dispensing station.

Platen identification information from the platen identifier 60 is read and/or written by the platen identifier I/O 165 and the platen identification information is provided to the main program 400 running on the controller 500 (see FIG. 12). In some embodiments, the platen identification information is used to determine which specific platen software program 402 needs to be used/loaded by the main program 402. In some embodiments, the platen identification information contains parameters that are used by a generic platen software program 402 to control the positioning of the platen 40 during filling operations. In some embodiments, the platen identification information contains the platen software program 402 and the platen software program 402 is read from the platen identifier 60 and loaded by the main program 402. As an example of a platen-specific program, if a given platen has one row of seven blisters, the platen specific program 402 is loaded/run to control the X-Y table 200 to place pills in that specific blister package. As an example of a generic platen program for a platen that has one row of seven blisters, the generic platen program 402 is provided control information from the platen identification information indicating, for example, valid positions on the platen where blisters (or vials) are present so that the X-Y table 200 is instructed to locate the blister package correctly when dispensing pills. In some embodiments, the platen identifier 60 is writable. For example, an external device pre-writes a pill count to the platen identifier 60 and the pill count is read by the platen identifier I/O and available to the main program 400. In another example, the number of times that the platen 40/41/44/48 is used is read, incremented, and then written back to the platen identifier 60 under control of the Platen I/O 165. The later is used, for example, in billing for usage or for determining wear rates and life-cycle data for the platens.

Referring to FIG. 12, a controller of the dispensing station of the present invention is shown. The controller 500 is shown for completeness and the device shown is a simplified example of a typical processor-based controller that has a processor 510 and associated memory 520 and storage 525. The storage 525 is, for example, Flash memory, battery-backed SRAM or a hard disk. This is an exemplary system and any suitable processor, memory and persistent storage can be substituted including microcontrollers such as the Intel® 80C51, processors such as the Intel® Pentium IV, memory such as SDRAM and DDR and persistent storage such as ROM, EPROM, hard disks, etc. The operating program 400, data parameters, etc. are typically stored in the persistent storage 525 A system bus 530 interfaces the processor to peripheral devices as discussed below.

The controller 500 displays information, alerts, prompts, etc., on a display 560. In some embodiments, the display 560 is a graphics display. In some embodiments, the display 560 is a LCD display. In other embodiments, the display is a numeric display, alpha-numeric display, set of lights or any combination thereof. Operation of the system is initiated by control inputs 570. In some embodiments, the control inputs 570 include a keyboard. In other embodiments, the control 570 includes push buttons, switches, potentiometers and digital potentiometers, etc.

The processor 510 reads and/or reads/writes the platen identification 60 through a platen reader input-output port 540 as known in the industry. The canister identification 160 is read and/or written by the processor 510 through a canister identification I/O port 550.

The X-Y motors 218/238 of the X-Y table 200 are controlled by an X/Y I/O port 580 and the carousel rotation motor 584 (or other selection mechanism motor control) is controlled by the carousel I/O port 582. The carousel dispensing motor 102 is controlled by a pill drive I/O port 586. In some embodiments (not shown) a pill drop sensor is connected to the processor 510 for counting the number of pills dropped at the target location.

Figure 13:
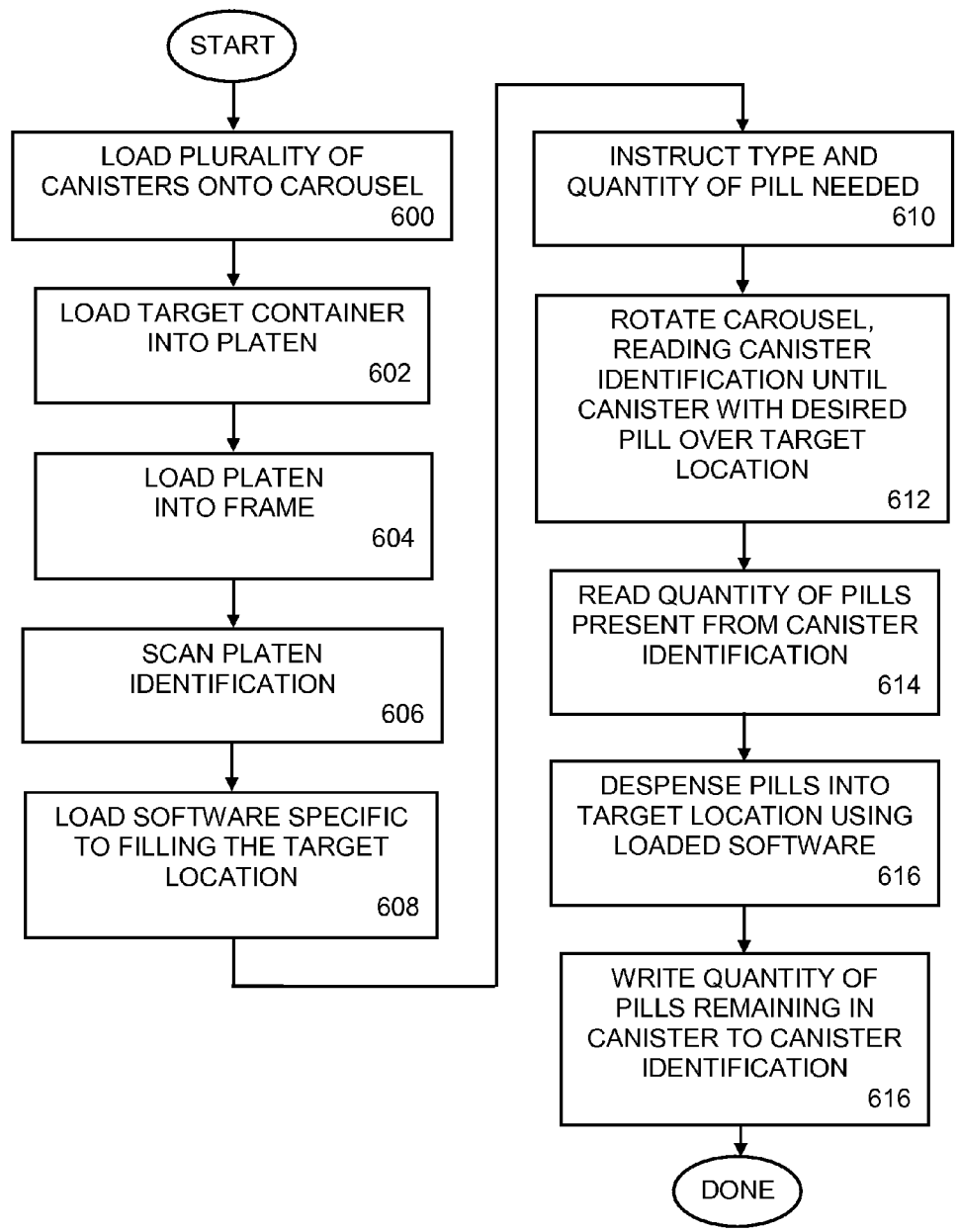
FIG. 13 illustrates a flow chart of the dispensing station.

Referring to FIG. 13, a flow chart of the dispensing station of the present invention is shown. This is one possible method of dispensing pills and various other methods and/or orders of steps are anticipated.

The method begins with loading 600 a plurality of canisters 100 onto the carousel 105 (or other canister selecting mechanism as previously described). Next, the desired target package (e.g., a specific blister pack or a vial) is loaded 602 into a platen configured to hold and support that type of package and the platen with the target package is loaded 604 into the frame 250 of the pill dispensing station 20 and the platen identification 60 is read 606 to determine which platen was loaded. Responsive to the platen identification 60, software specific to filling that platen is loaded/run 608. Next, the request (e.g., type of pill, quantity of pills and distribution within the individual blisters) is entered 610 (or prescription scanned at the dispensing station scanner 18). The canister 107 having the desired pill type is selected and placed over the target location 612. In some embodiments, the canister identification 160 is read to assure/determine the proper canister 107 is located over the target location. In some embodiments, the current quantity of pills present in the canister 107 is read 614 from the canister identification 160 to assure a sufficient number of pills are available in the canister 107. The desired pills are dispensed into the target location 616, moving the X-Y table as per the software 402 specific to the particular platen to fill individual blisters as needed. In embodiments in which the canister identification 160 is writeable, an updated quantity of pills contained within the canister 107 is written 616 to the canister identification 160.

Equivalent elements can be substituted for the ones set forth above such that they perform in substantially the same manner in substantially the same way for achieving substantially the same result.

It is believed that the system and method of the present invention and many of its attendant advantages will be understood by the foregoing description. It is also believed that it will be apparent that various changes may be made in the form, construction and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. A device for dispensing pills, the device comprising:
a plurality of pill canisters, each of the pill canisters containing pills;
a plurality of platens, each of the platens being substantially planar, each of the plurality of platens having a platen identifier, each of the platens having pill locations corresponding to one or more specific packaging configurations;
a selected platen of the platens, the selected platen removably holds and supports a target container;
a frame situated beneath the target location, the selected platen is removably and interchangeably held in the frame and the selected platen moves in both an X axis and/or a Y axis responsive to movement of the frame moving in both the X axis and/or the Y axis;

a device for communicating with the platen identifier; and a control, the control accesses the device for communicating with the platen identifier and obtains data from the platen identifier, the control moves the selected platen in the X axis and the Y axis responsive to the data and the control releases a desired quantity of the pills at a target location into the a target package that is held by the selected platen.

2. The device for dispensing pills of claim 1, wherein the platen identifier is an RFID.

3. The device for dispensing pills of claim 1, wherein the platen identifier is a readable and writeable device having writable data storage.

4. The device for dispensing pills of claim 3, wherein the quantity of pills is written into the writable data storage before the platen is placed in the frame.

5. The device for dispensing pills of claim 4, wherein the data includes the quantity of pills.

6. A method for dispensing pills, the method comprising:
providing a device for dispensing pills comprising:
a plurality of pill canisters, each of the pill canisters containing pills;
a plurality of platens, each of the platens being substantially planar, each of the plurality of platens having a platen identifier, each of the platens having pill locations corresponding to one or more specific packaging configurations;
a frame situated beneath the target location, any of the platens is removably and interchangeably held by the frame and the frame moves in both an X axis and/or a Y axis responsive to a control;
a device for communicating with the platen identifier, the device interfaced to the control;
selecting a first target package;
selecting a first platen from the plurality of platens, the first platen configured to hold and support the first target package;
placing the first target package into the first platen;
inserting the first platen into the frame;
the control reading data from the platen identifier;
using the data, the control moves the frame and first platen in the x-axis and the y-axis and the control dispenses pills into the first target package in x-axis and y-axis locations as determined by the data;
removing the first platen from the frame;
removing the first target package from the first platen;
selecting a second target package;
selecting a second platen from the plurality of platens, the second platen configured to hold and support the second target package;
placing the second target package into the second platen;
inserting the second platen into the frame;
the control reading data from the platen identifier of the second platen;
using the data, the control moves the frame and second platen in the x-axis and the y-axis and the control dispenses pills into the second target package in x-axis and y-axis locations as determined by the data;
removing the second platen from the frame;
removing the second target package from the second platen.

7. The method of claim 6, wherein the platen identifier is an RFID.

8. The method of claim 6, wherein the platen identifier is readable and writeable.

9. The method of claim 8, wherein the data includes a quantity of pills and the steps of using the data further comprises using the quantity of pills to dispense the quantity of pills into the first and second target package.

10. A device for dispensing pills, the device comprising:
a plurality of pill canisters, each canister containing a quantity of pills;
a controller;
a means for selecting a source pill canister from the plurality of pill canisters by direction of the controller;
a means for releasing a desired quantity of the pills from the source pill canister by direction of the controller, the desired quantity of the pills released at a target location;
a plurality of platens, each platen having a means for identification, each of the platens being substantially planar;
an active platen selected from the plurality of platens and held in a frame, the frame moves the active platen in both an X axis and/or a Y axis by direction of the controller and the frame positions the active platen beneath the target location, whereas the active platen is removably held by the frame; and
a device for interfacing with the means for identification, the device communicatively connected to the controller.

11. The device for dispensing pills of claim 10, wherein the means for identification is an RFID and the device for reading the means for identification is an RFID reader.

12. The device for dispensing pills of claim 10, wherein the means for identification has writeable storage.

13. The device for dispensing pills of claim 12, wherein the controller reads the quantity of pills from the means for identification.

14. The device for dispensing pills of claim 13, wherein the quantity of pills is written to the means for identification before the active platen is held in the frame.

* * * * *